US010265023B2

(12) United States Patent
Roh et al.

(10) Patent No.: US 10,265,023 B2
(45) Date of Patent: Apr. 23, 2019

(54) LASER SPECKLE CONTRAST IMAGING SYSTEM, LASER SPECKLE CONTRAST IMAGING METHOD, AND APPARATUS INCLUDING THE LASER SPECKLE CONTRAST IMAGING SYSTEM

(71) Applicants: SAMSUNG ELECTRONICS CO., LTD., Suwon-si (KR); SEOUL NATIONAL UNIVERSITY R&DB FOUNDATION, Seoul (KR)

(72) Inventors: Younggeun Roh, Seoul (KR); Byoungho Lee, Seoul (KR); Jiwoon Yeom, Suwon-si (KR); Youngmo Jeong, Seoul (KR); Jinsoo Jeong, Seoul (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 317 days.

(21) Appl. No.: 15/184,655

(22) Filed: Jun. 16, 2016

(65) Prior Publication Data

US 2017/0017858 A1    Jan. 19, 2017

(30) Foreign Application Priority Data

Jul. 15, 2015  (KR) .................. 10-2015-0100515

(51) Int. Cl.
*A61B 5/026* (2006.01)
*A61B 5/00* (2006.01)
(Continued)

(52) U.S. Cl.
CPC .......... *A61B 5/7207* (2013.01); *A61B 5/0261* (2013.01); *G02B 21/0008* (2013.01);
(Continued)

(58) Field of Classification Search
CPC ........................ A61B 5/7207; A61B 5/0261
See application file for complete search history.

(56) References Cited

U.S. PATENT DOCUMENTS 8,585,206 B2  11/2013 Gollier
9,931,040 B2 *  4/2018 Homyk ............... A61B 5/0075
(Continued)

FOREIGN PATENT DOCUMENTS

JP              4769952 B2   9/2011
KR    10-2010-0042648 A    4/2010

OTHER PUBLICATIONS

Andrew K. Dunn et al; "Dynamic Imaging of Cerebral Blood Flow Using Laser Speckle"; Journal of Cerebral Blood Flow and Metabolism; vol. 21; 2001; pp. 195-201.
(Continued)

*Primary Examiner* — George R Evanisko
(74) *Attorney, Agent, or Firm* — Sughrue Mion, PLLC (57) ABSTRACT

Provided are a laser speckle contrast imaging method, a laser speckle contrast imaging system, and an apparatus which includes the laser speckle contrast imaging system. The laser speckle contrast imaging system includes a laser light source configured to irradiate laser beams toward a subject, the laser beams having a plurality of wavelength bands and different surface transmittances with respect to the subject. An imaging unit is configured to acquire speckle images by capturing images of speckles by using an image sensor, the speckles being formed when the irradiated laser beams are scattered from the subject. A signal processor is configured to convert the acquired speckle images into speckle contrast images and to acquire a compensated speckle contrast image by compensating for a change caused by a movement of the subject.

16 Claims, 8 Drawing Sheets

(51) Int. Cl.
*G02B 27/48* (2006.01)
*G02B 21/00* (2006.01)
G02B 13/00 (2006.01)
G06K 9/00 (2006.01)
G02B 13/14 (2006.01)

(52) U.S. Cl.
CPC ............ *G02B 27/48* (2013.01); *A61B 5/6898* (2013.01); *G02B 13/009* (2013.01); *G02B 13/146* (2013.01); *G06K 9/0012* (2013.01); *G06K 2009/00932* (2013.01)

(56) References Cited

U.S. PATENT DOCUMENTS

| | | | |
|---|---|---|---|
| 2010/0168585 A1 | 7/2010 | Fujii et al. | |
| 2011/0013002 A1 | 1/2011 | Thompson et al. | |
| 2011/0178397 A1 | 7/2011 | Bahner | |
| 2012/0162438 A1* | 6/2012 | Thakor | A61B 5/0062 348/161 |
| 2013/0204112 A1 | 8/2013 | White et al. | |
| 2015/0043770 A1* | 2/2015 | Chen | G06K 9/00208 382/103 |
| 2016/0157736 A1* | 6/2016 | Huang | A61B 5/0059 600/477 |
| 2016/0270672 A1* | 9/2016 | Chen | A61B 5/0261 |

OTHER PUBLICATIONS

Guillaume Mahe et al; "Laser speckle contrast imaging accurately measures blood flow over moving skin surfaces"; Microvascular Research; vol. 81; 2011; pgs. 183-188.

Nan Li et al; "High spatiotemporal resolution imaging of the neurovascular response to electrical stimulation of rat peripheral trigeminal nerve as revealed by in vivo temporal laser speckle contrast"; Journal of Neuroscience Methods; vol. 176; 2009; pp. 230-236.

Andrew M. Smith et al; "Second window for in vivo imaging"; Nature Nanotechnology; vol. 4; Nov. 2009; pp. 710-711.

Yang Liu et al; "Investigation of depth selectivity of polarization gating for tissue characterization"; Optics Express; vol. 13; No. 2; Jan. 24, 2005; pp. 601-611.

* cited by examiner

LASER SPECKLE CONTRAST IMAGING SYSTEM, LASER SPECKLE CONTRAST IMAGING METHOD, AND APPARATUS INCLUDING THE LASER SPECKLE CONTRAST IMAGING SYSTEM

CROSS-REFERENCE TO RELATED APPLICATION

This application claims priority from Korean Patent Application No. 10-2015-0100515, filed on Jul. 15, 2015, in the Korean Intellectual Property Office, the disclosure of which is incorporated herein by reference in its entirety.

BACKGROUND

1. Field

Exemplary embodiments relate to laser speckle contrast imaging methods, laser speckle contrast imaging systems, and apparatuses including the laser speckle contrast imaging systems.

2. Description of the Related Art

Laser speckle contrast imaging is a technology for measuring or imaging a fine change or a flow rate of a target subject by using a laser light source which is capable of generating speckles. The laser speckle contrast imaging may generate speckles by using a light source having a single wavelength band, and may image the generated speckles by using one speckle-generating light source and one speckle imaging device. A flow rate at a target position may be recorded or imaged, taking into consideration a degree of temporal or spatial distribution of speckle images generated by a laser light source.

Since the general laser speckle contrast imaging does not assume a global movement of a target subject, the general laser speckle contrast imaging is used in a state in which external movements, except for the target subject, are completely excluded. Due to the limiting condition, when a target blood vessel or a spot through which a fluid flows, which is to be imaged, shakes or moves due to an external influence, noise exists within the resulting imaged contrast information. Therefore, it is difficult to apply the general laser speckle contrast imaging to a blood flow rate measurement through imaging of the skin of a human body or an animal that is not anesthetized.

SUMMARY

Provided are laser speckle contrast imaging systems and a laser speckle contrast imaging method, which are capable of compensating for noise caused by a movement of a subject.

Provided are apparatuses including the laser speckle contrast imaging systems.

Additional aspects will be set forth in part in the description which follows and, in part, will be apparent from the description, or may be learned by practice of the presented exemplary embodiments.

According to an aspect of an exemplary embodiment, a laser speckle contrast imaging system includes: a laser light source configured to irradiate laser beams toward a subject, each of the laser beams having a respective wavelength band and a respective surface transmittance with respect to the subject; an image capturer configured to acquire speckle images by capturing images of speckles by using an image sensor, the speckles being formed when the irradiated laser beams are scattered from the subject; and a signal processor configured to convert the acquired speckle images into at least one speckle contrast image and to acquire a compensated speckle contrast image by compensating for a change caused by a movement of the subject.

The subject may have a fluid tube through which a fluid flows, and the laser light source may include: a first laser light source component configured to emit a first laser beam which has a first wavelength band and which propagates through a surface of the subject and is scattered by the fluid; and a second laser light source component configured to emit a second laser beam which has a second wavelength band and which is scattered from the surface of the subject, wherein the signal processor is further configured to acquire a first speckle contrast image from a scattering of the laser beam, and to acquire a second speckle contrast image from a scattering of the second laser beam.

The first speckle contrast image may be usable for acquisition of desired information, the second speckle contrast image may be usable for compensation of noise, and the signal processor may be further configured to acquire a third speckle contrast image showing a change in a fluid amount by compensating for noise included in the first speckle contrast image due to the movement of the subject by using the second speckle contrast image.

The subject may include a subject that has a blood vessel, and the signal processor may be further configured to acquire a fourth speckle contrast image which shows a change in a blood flow in the blood vessel of the subject.

The first wavelength band may include a near-infrared light wavelength band, and the second wavelength band may include a blue light wavelength band.

The first wavelength band may include a near-infrared light wavelength band, and the second wavelength band may include a blue light wavelength band.

The image capturer may be further configured to acquire a corresponding speckle image with respect to each respective wavelength band.

The image capturer may be further configured to acquire a corresponding speckle image with respect to each respective wavelength band.

The signal processor may be further configured to execute a noise compensation algorithm that compensates for noise caused by the movement of the subject.

The signal processor may be further configured to acquire a first speckle contrast image which is usable for acquisition of desired information and a second speckle contrast image which is usable for compensation of noise from the speckle images acquired by the image capturer, and the noise compensation algorithm may compensate the first speckle contrast image by using the second speckle contrast image in a circumstance in which a correlation between the first speckle contrast image and the second speckle contrast image exceeds a predetermined threshold.

The laser speckle contrast imaging system may further include an imaging lens optical system configured to adjust a magnification such that at least one from among the speckle images acquired by the image capturer becomes larger in size than a pixel of the image sensor.

The imaging lens optical system may be configured to adjust the magnification such that the at least one from among the speckle images acquired by the image capturer has at least twice the size of the pixel of the image sensor.

According to an aspect of another exemplary embodiment, an apparatus includes the laser speckle contrast imaging system.

The apparatus may include a mobile device that is mounted with the laser light source and the image capturer and is embedded with the signal processor.

The mobile device may include at least one from among a mobile phone, a smart phone, a wristwatch-type device, a tablet device, a personal digital assistant (PDA), a laptop computer, a head mounted display, and a portable media player.

The apparatus may include a medical imaging apparatus.

According to an aspect of another exemplary embodiment, a laser speckle contrast imaging method includes: irradiating laser beams toward a subject, each of the laser beams having a respective wavelength band and a respective surface transmittance with respect to the subject; acquiring speckle images by capturing images of speckles by using an image sensor, the speckles being formed when the irradiated laser beams are scattered from the subject; converting the acquired speckle images into at least one speckle contrast image; and acquiring a compensated speckle contrast image by compensating for a change caused by a movement of the subject.

The subject may include a subject that has a blood vessel, and the method may further include acquiring a first speckle contrast image which is usable for acquisition of information that relates to a change in a blood flow and a second speckle contrast image which is usable for compensation of noise caused by the movement of the subject by irradiating, toward the subject, a first laser beam which has a near-infrared light wavelength band and which propagates through a surface of the subject and is scattered by the blood flow in the blood vessel, and by irradiating, toward the subject, a second laser beam which has a blue light wavelength band and which is scattered from the surface of the subject, and a noise compensation algorithm for compensating for the noise caused by the movement of the subject may be applied in order to compensate the first speckle contrast image by using the second speckle contrast image in a circumstance in which a correlation between the first speckle contrast image and the second speckle contrast image exceeds a predetermined threshold.

The laser speckle contrast imaging method may further include performing an adjustment such that at least one from among the acquired speckle images becomes larger in size than a pixel of the image sensor.

The adjustment may be performed such that the at least one from among the acquired speckle images has at least twice the size of the pixel of the image sensor.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. The sizes of the elements may be exaggerated for clarity and convenience of description. The following exemplary embodiments are merely exemplary and various modifications may be made thereto.

It will be understood that when an element is referred to as being "disposed on" another element, it may be directly or indirectly disposed on the other element. In this aspect, for example, intervening elements may be present.

It will be understood that, although the terms "first", "second", etc. may be used herein to describe various elements, these elements should not be limited by these terms. These terms are only used to distinguish one element from another element.

As used herein, the singular forms "a," "an" and "the" are intended to include the plural forms as well, unless the context clearly indicates otherwise. It will also be understood that the terms "comprises", "includes", and "has", when used herein, specify the presence of stated elements, but do not preclude the presence or addition of other elements, unless otherwise defined.

Further, the terms "unit" and "module" used herein represent a unit for processing at least one function or operation, which may be implemented by hardware, software, or a combination of hardware and software.

In the present disclosure, the term "target subject" as used herein means a subject for which a biological condition is to be measured, and the subject may be an animal or a human being. In addition, the term "user" as used herein may be a target subject, that is, a subject from which a biosignal is to be measured, but the user may be any medical expert having the ability to operate a biosignal processing apparatus. In particular, the user may be a broader concept than a target subject.

A laser speckle contrast imaging system according to an exemplary embodiment may use at least two laser light sources to generate speckles by irradiating, toward a subject, laser beams which encompass a plurality of wavelength bands and which have different surface transmittances. A speckle image with respect to a laser beam which has at least one wavelength band may be used to acquire desired information, and speckle images with respect to the other laser beam which has at least one wavelength band may be used to remove noise generated by an undesired movement. The subject may be any subject that has a fluid tube through which a fluid flows. For example, the subject may be any subject that has a blood vessel. The desired information may be a biosignal that relates to the amount of a fluid flowing through a fluid tube, for example, a blood flow rate in the blood vessel, and the laser speckle contrast imaging system according to the exemplary embodiment may be configured to capture an image of a subject in a contactless or noninvasive manner and to acquire a laser speckle contrast image in which noise caused by a movement of the subject is compensated for, or to quantify the laser speckle contrast image. In particular, when the subject has a blood vessel, the laser speckle contrast imaging system according to the exemplary embodiment may acquire information about a blood flow rate or the like as an image or a quantified amount. Hereinafter, for clarity of description, a case where a subject has a blood vessel will be described as an example, but the exemplary embodiment is not limited thereto. Laser beams having different wavelength bands may be applied according to a surface transmittance of the subject or a type of a fluid, and accurate information about a fluid amount may be acquired by compensating for noise caused by the movement of the subject. The movement of the subject having a blood vessel may include an external movement, a movement of the surface of the skin due to a muscle tremor, and the like.

Figure 1:
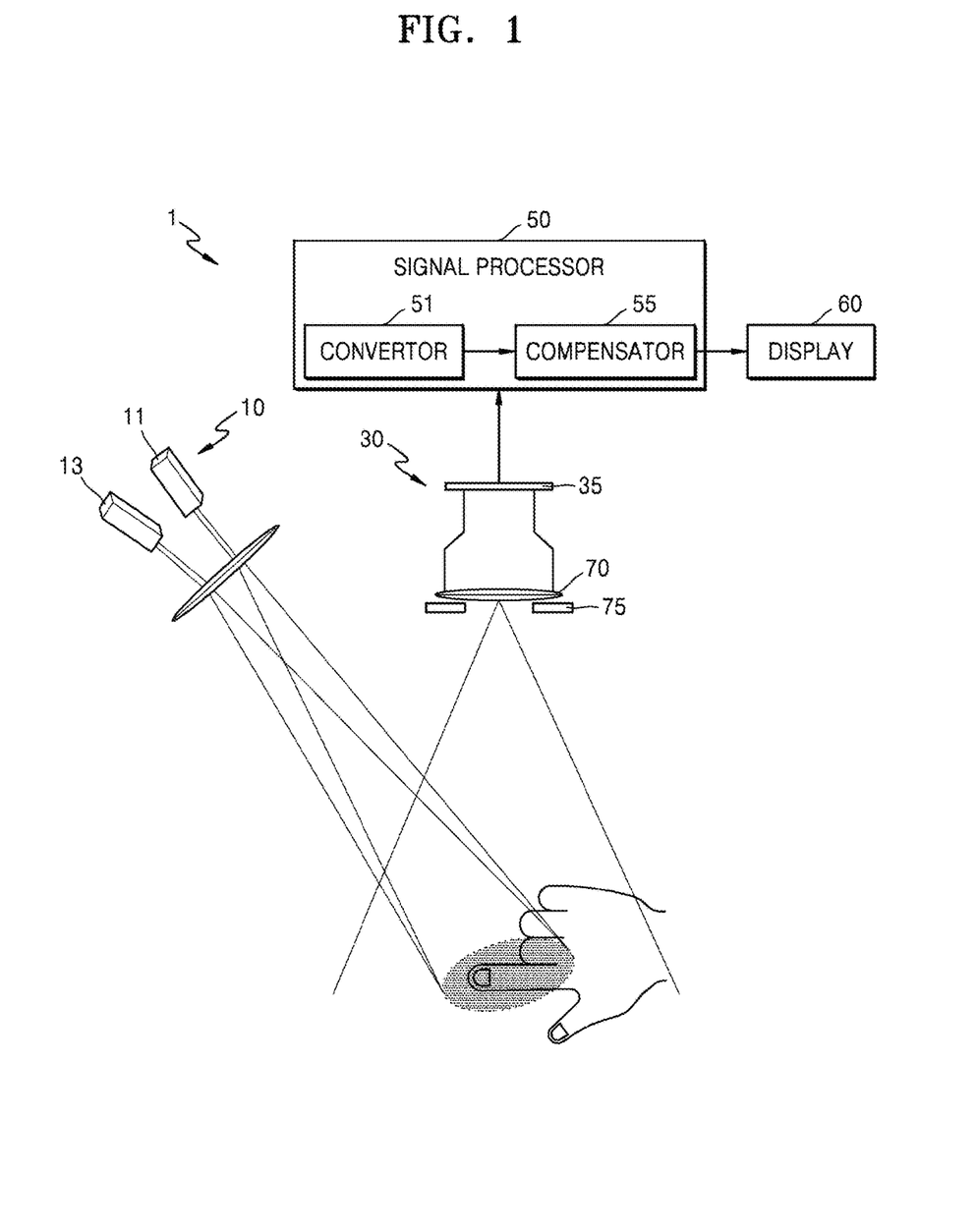
FIG. 1 is a diagram for describing a laser speckle contrast imaging system, according to an exemplary embodiment.

FIG. 1 is a diagram for describing a laser speckle contrast imaging system 1, according to an exemplary embodiment.

Referring to FIG. 1, the laser speckle contrast imaging system 1 according to the exemplary embodiment may include a laser light source 10, an imaging unit (also referred to herein as an "image capturer") 30, and a signal processor 50.

The laser light source 10 is configured to irradiate laser beams which encompass a plurality of wavelength bands and which have different respective surface transmittances with respect to a subject. The laser light source 10 may include a plurality of laser light sources, for example, a first laser light source component 11 and a second laser light source component 13, which emit laser beams having a plurality of wavelength bands and having different surface transmittances with respect to a subject. The laser light source 10 may include three or more laser light sources.

The first laser light source component 11 may be configured to emit a laser beam having a first wavelength band (e.g., near-infrared light wavelength band), which propagates through a surface of the subject and is mostly scattered by a blood flow in a blood vessel. The second laser light source component 13 may be configured to emit a laser beam having a second wavelength band (e.g., blue light wavelength band), which is mostly scattered from an outer surface of the subject, that is, the surface of the skin of the subject.

The laser speckle contrast imaging system 1 according to the exemplary embodiment may use the fact that materials under the skin have different absorption rates and scattering coefficients, for example, in the near-infrared light wavelength band and the blue light wavelength band. For example, an epidermis of the subject may have a thickness of about 100 μm, whereas a laser beam having a wavelength of about 450 nm may have a penetration depth of about 50 μm and a laser beam having a wavelength of about 780 nm may have a penetration depth of about 200 μm. The laser beam having a wavelength of about 780 nm is not absorbed into the blood and is scattered from the blood, thus exhibiting high reflectivity. A majority of the laser beam having a wavelength of about 450 nm may be scattered and reflected from the surface of the skin of the subject.

In the laser speckle contrast imaging system 1 according to the exemplary embodiment, a laser beam having a near-infrared light wavelength of, for example, about 780 nm, may be used as the laser beam having the first wavelength band, and a laser beam having a blue light wavelength of, for example, about 450 nm, may be used as the laser beam having the second wavelength band. The use of the laser beam having the wavelength of about 780 nm and the laser beam having the wavelength of about 450 nm is merely exemplary and the exemplary embodiment is not limited thereto. For example, laser beams having various wavelength bands and different skin transmittances may be applied to the laser speckle contrast imaging system 1.

The laser beam having the near-infrared light wavelength band, which is emitted from the first laser light source component 11, and the laser beam having the blue light wavelength band, which is emitted from the second laser light source component 13, may be irradiated toward the same or a similar position of the subject.

The imaging unit 30 may be configured to acquire speckle images by capturing images of speckles by using an image sensor 35, the speckles being formed when the irradiated laser beams are scattered from the subject. The imaging unit 30 may be configured to acquire speckle images with respect to the respective wavelength bands. For example, the imaging unit 30 may acquire a first speckle image and a second speckle image by imaging the subject via the image sensor 35. The first speckle image may be acquired by the scattering of the laser beam having the near-infrared light wavelength band, which is irradiated on the subject from the first laser light source 11, and the second speckle image may be acquired by the scattering of the laser beam having the blue light wavelength band, which is irradiated on the subject from the second laser light source 13. In the case of using the laser beam having the near-infrared light wavelength band and the laser beam having the blue light wavelength band, the image sensor 35 may be a general color image sensor capable of acquiring, for example, a red color (R) image, a green color (G) image, and a blue color (B) image. In this aspect, the R image and the B image acquired by the general color image sensor may correspond to the first speckle image and the second speckle image, respectively. The image sensor 35 may have various structures. For example, the image sensor 35 may have a structure which includes a monochrome color image sensor and a color filter that is disposed at a front end of the monochrome color image sensor and has an arrangement of filter elements which respectively transmit the first and second wavelength bands.

The signal processor 50 may be configured to convert the speckle images acquired by the imaging unit 30 into one or more speckle contrast images. In addition, the signal processor 50 may be configured to execute a noise compensation algorithm so as to compensate for a change caused by the movement of the subject and thereby acquire a compensated speckle contrast image. To this end, the signal processor 50 may include a converter 51 configured to convert the speckle image acquired by the imaging unit 30 into the speckle contrast image, and a compensator 55 configured to acquire the speckle contrast image compensated by using the noise compensation algorithm. The movement of the subject may include any of an external movement, a tremor of the surface of the skin of the subject due to a muscle tremor, and the like.

The signal processor 50 may be configured to convert the speckle image, which is acquired by the scattering of the laser beam having the first wavelength band, into a first speckle contrast image, and may be configured to convert the speckle image, which is acquired by the scattering of the laser beam having the second wavelength band, into a second speckle contrast image. The first speckle contrast image may be a speckle contrast image which is usable for acquisition of desired information, and the second speckle contrast image may be a speckle contrast image which is usable for compensation of noise. The signal processor 50 may be configured to compensate for the noise of the first speckle contrast image, which noise is caused by the movement of the subject, by using the second speckle contrast image, and to acquire a speckle contrast image which indicates a physiological signal, for example, a change in a blood flow rate, or to quantify the speckle contrast image. The acquired speckle contrast image or the quantification result may be displayed as an image on a display 60.

The noise compensation algorithm may be configured to compensate the speckle contrast image that is usable for the acquisition of the desired information by using the speckle contrast image that is usable for the compensation of the noise in a section in which a correlation between the speckle contrast image for the acquisition of the desired information and the speckle contrast image for the compensation of the noise is relatively strong, i.e., a correlation which exceeds a predetermined threshold correlation value. An exemplary embodiment of the noise compensation algorithm applied to the signal processor 50 will be described below.

The laser speckle contrast imaging system 1 according to the exemplary embodiment may further include an imaging lens optical system 70 configured to adjust a magnification such that an image of the speckle imaged by the imaging unit 30 has a meaningful size. An aperture 75 may be disposed in front of the imaging lens optical system 70.

The imaging lens optical system 70 may adjust the magnification such that the image of the speckle imaged by the imaging unit 30 becomes larger in size than a pixel of the image sensor 35. For example, the imaging lens optical system 70 may adjust the magnification so that the image of the speckle imaged by the imaging unit 30 has approximately twice the size of the pixel of the image sensor 35 or slightly larger or less than twice the size of the pixel of the image sensor 35. When the image size of the speckle is excessively large, a spatial resolution becomes small. The spatial resolution corresponds to an ability to analyze an image by using the speckle. The imaging lens optical system 70 may adjust the magnification so that the image of the speckle has an appropriate size in a range satisfying a condition of the spatial resolution.

For example, the speckle image may be adjusted to have about twice the size of the pixel of the image sensor 35 based on Formula 1 below.

$$\rho_{speckle} = 2.44\lambda(1+M_{cam})f/\# \quad \text{[Formula 1]}$$

$\rho_{speckle}$ is an image size of one speckle at the time of imaging (i.e., image capturing), $\lambda$ is a wavelength used at the time of imaging, $M_{cam}$ is a magnification of the imaging unit 30 used at the time of imaging, and f/# is an F-value of the imaging unit 30.

The speckle image acquired by the imaging unit 30 may be converted into a speckle contrast image by the signal processor 50, as expressed in Formula 2 below.

$$K(x, y) = \frac{\sigma_N}{\mu_N} \quad \text{[Formula 2]}$$

$K(x,y)$ is an acquired speckle contrast, $\sigma_N$ is a standard deviation of N elements made in order to acquire a contrast, and $\mu_N$ is an average of the N elements. Each of the N elements may be selected in a window form in a spatial domain or may be selected in a time domain. For example, $\sigma_N$ may be a standard deviation of a target pixel and N pixels adjacent thereto. In addition, for example, $\mu_N$ may be an average of the target pixel and the N pixels adjacent thereto.

In the extracting of the speckle contrast in the spatial domain, since the speckle contrast is extracted by dividing the captured image into small windows, a time-series resolution may be relatively high but a spatial resolution may be relatively low. In the extracting of the speckle contrast in the time domain, since the speckle contrast is extracted between the pixels located at the same position of speckle images recorded with time, a time-series resolution may be relatively low but a spatial resolution may be relatively high. The extracting of the speckle contrast in the time domain may exhibit relatively good characteristics in a condition of noise generation such as a tremor, as compared to the extracting of the speckle contrast in the spatial domain.

As described above, the laser speckle contrast imaging system 1 may use the noise compensation algorithm that removes the noise generated together with a desired signal through the speckle contrasts with respect to two wavelength bands having different transmittances on the surface of the subject. The noise compensation algorithm may be implemented by using a sample correlation coefficient between two or more imaged speckle contrasts and a reference speckle contrast value. Formula 3 below may be used for obtaining a sample correlation coefficient between speckle contrast images recorded with respect to two different wavelength bands. In Formula 3, $K_1$ is a laser speckle contrast value with respect to a specific wavelength, and $K_2$ is a laser speckle contrast value with respect to a wavelength different from the specific wavelength.

$$C = \frac{\sum (K_1 - \overline{K_1}) \cdot (K_2 - \overline{K_2})}{\sqrt{\sum (K_1 - \overline{K_1})^2 \cdot \sum (K_2 - \overline{K_2})^2}} \quad \text{[Formula 3]}$$

When the laser speckle contrast image with respect to a wavelength band used for acquiring desired information records a smaller amount of contrast than a reference speckle contrast, it may be determined through the proposed noise compensation algorithm that external noise or the desired information has been introduced. In this circumstance, in a case where a correlation with the laser speckle contrast information used for the compensation of the noise is relatively high, it may be determined that the external noise is dominant and, for example, the recorded speckle contrast value may be compensated for based on Formula 4 below. In Formula 4, $K_{com}$ is a compensated speckle contrast value, $K_1$ is a speckle contrast value with respect to a laser beam used for recording of the information, $K_2$ is a speckle contrast value of a laser beam used for the compensation of the noise, and $\beta$ is a compensation coefficient.

$$K_{com} = K_1 + \beta \cdot K_2 \quad \text{[Formula 4]}$$

When the laser speckle contrast image with respect to the wavelength band used for the acquisition of the desired information records a smaller amount of contrast than the reference speckle contrast but the sample correlation coefficient is not greater than a reference correlation coefficient, the speckle may not be compensated for based on Formula 4. Formula 4 is merely one example. Instead of determining the reference correlation coefficient, a method of compensating the speckle by using different compensation coefficients according to the sample correlation coefficient may be used as expressed in Formula 5 below. In this case, the compensation coefficient β may be expressed as a function of a sample correlation coefficient C.

$$K_{com} = K_1 + \beta(C) \cdot K_2 \quad \text{[Formula 5]}$$

Figure 2:
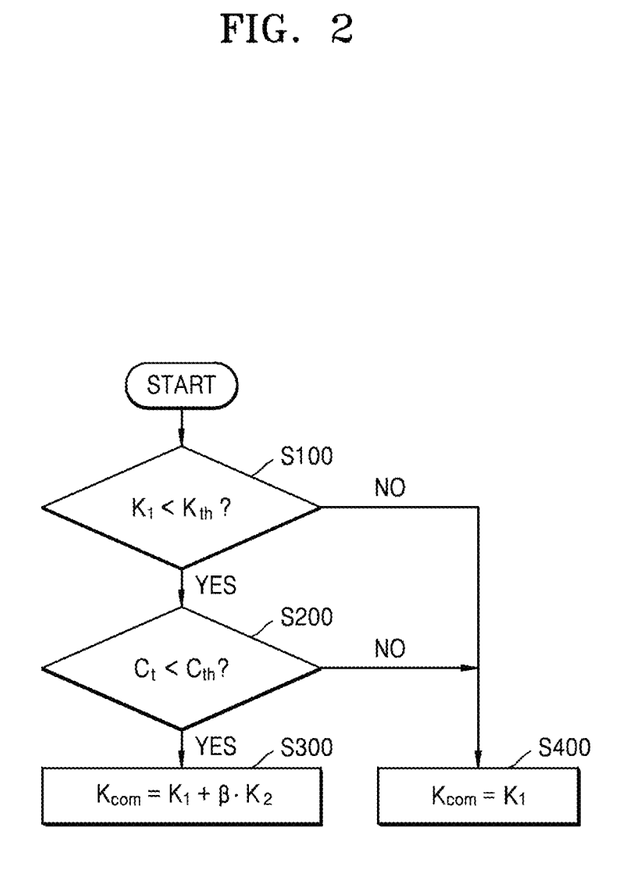
FIG. 2 is a flowchart of a speckle contrast noise compensation algorithm using laser beams that have different surface transmittances, according to an exemplary embodiment.

FIG. 2 is a flowchart of a speckle contrast noise compensation algorithm which is applicable for laser beams that have different surface transmittances, according to an exemplary embodiment. In FIG. 2, $C_{th}$ and $K_{th}$ respectively indicate a reference correlation coefficient and a reference speckle contrast and may be determined according to an imaging environment.

Referring to FIG. 2, in operation S100, it may be determined whether a speckle contrast value $K_1$ with respect to a laser beam that is usable for acquisition of desired information, which value is obtained by the signal processor 50, is less than a reference speckle contrast value $K_{th}$.

In operation S400, when the speckle contrast value $K_1$ is greater than the reference speckle contrast value $K_{th}$, the speckle contrast value $K_1$ may be used as a compensated speckle contrast value $K_{com}$.

In operation S200, when the speckle contrast value $K_1$ is less than the reference speckle contrast value $K_{th}$, it may be determined whether a sample correlation coefficient $C_t$ between speckle contrast images recorded with respect to two wavelength bands is less than a reference correlation coefficient $C_{th}$.

In operation S400, when the sample correlation coefficient $C_t$ is greater than the reference correlation coefficient $C_{th}$, the speckle contrast value $K_1$ may be used as the compensated speckle contrast value $K_{com}$.

In operation S300, when the sample correlation coefficient $C_t$ is less than the reference correlation coefficient $C_{th}$, the compensated speckle contrast $K_{com}$ may be obtained by compensating for the speckle contrast value $K_1$ by using the speckle contrast value $K_2$ of the laser beam used for compensation of noise by using the compensation coefficient β as expressed in Formulas 4 and 5. The case of obtaining the compensated speckle contrast $K_{com}$ based on Formula 4 is illustrated in FIG. 2, but Formula 5 may be applied instead of Formula 4.

As described above, the laser speckle contrast imaging system 1 according to the exemplary embodiment may complement a limitation that the general laser speckle contrast imaging which uses a single laser light source is vulnerable to noise caused by the movement of the subject. In addition, since the laser speckle contrast imaging system 1 according to the exemplary embodiment does not need strong computing power, the laser speckle contrast imaging system 1 may also be used so as to acquire a biosignal by using a mobile device or the like. Furthermore, the laser speckle contrast imaging system 1 according to the exemplary embodiment may also be easily and additionally applied to apparatuses which include the existing laser speckle contrast imaging system.

In the laser speckle contrast imaging system 1 according to the exemplary embodiment, the signal processor 50 may be installed in a separate processing apparatus (e.g., computer system) which is capable of being connected to the imaging unit 30 by wired communication or by wireless communication, such as Bluetooth, or may be installed in a device (e.g., mobile device) which is mounted with the laser light source 10 and the imaging unit 30.

For example, an apparatus which include the laser speckle contrast imaging system 1, according to an exemplary embodiment, may be a mobile device mounted with the laser light source 10 and the imaging unit 30 and embedded with the signal processor 50, or may be a medical imaging apparatus which is connected to the imaging unit 30 by wire or wirelessly. Examples of the mobile device may include any of a mobile phone, a smart phone, a wristwatch-type device, a tablet device, a personal digital assistant (PDA), a laptop computer, a head mounted display, and a portable media player.

Figure 3:
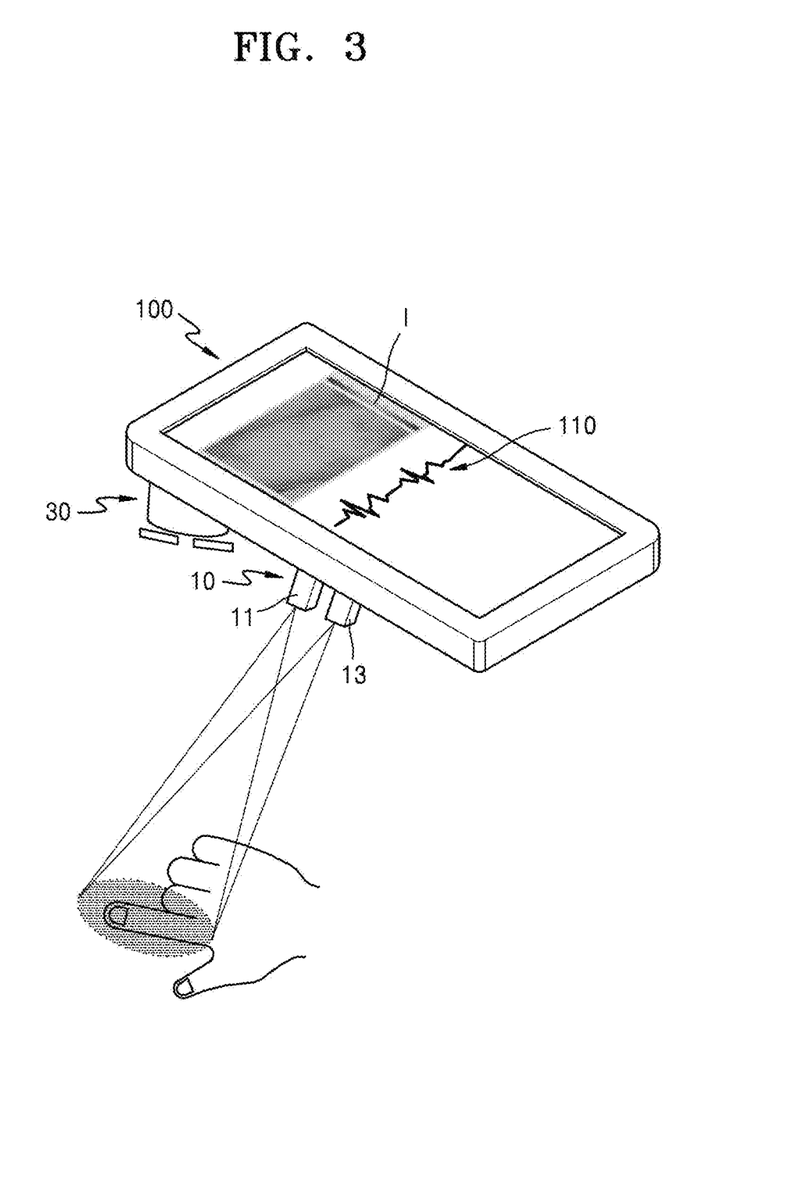
FIG. 3 is a diagram for describing an exemplary embodiment in which the laser speckle contrast imaging system of FIG. 1 is applied to a smart phone as one of mobile devices.

FIG. 3 is a diagram illustrating an exemplary embodiment in which the laser speckle contrast imaging system 1 of FIG. 1 is applied to a mobile device 100 (e.g., a smart phone).

Referring to FIG. 3, the mobile device 100 may be mounted with the laser light source 10 and the imaging unit 30 and may be embedded with the signal processor 50. In addition, a speckle contrast image I acquired by the signal processor 50 may be displayed as an image on a display 110 of the mobile device 100.

In a case where the laser speckle contrast imaging system 1 according to the exemplary embodiment is applied to the mobile device 100, the display unit 60 of FIG. 1 may correspond to the display 110 of the mobile device 100.

As described above, a biosignal (e.g., blood flow rate) may be measured in a contactless or noninvasive manner by applying the laser speckle contrast imaging system 1 to the mobile device 100.

The following description relates to the principle of acquiring the speckle contrast image, in which noise caused by an external movement is compensated for, by using the laser speckle contrast imaging system 1 according to the exemplary embodiment.

Figure 4:
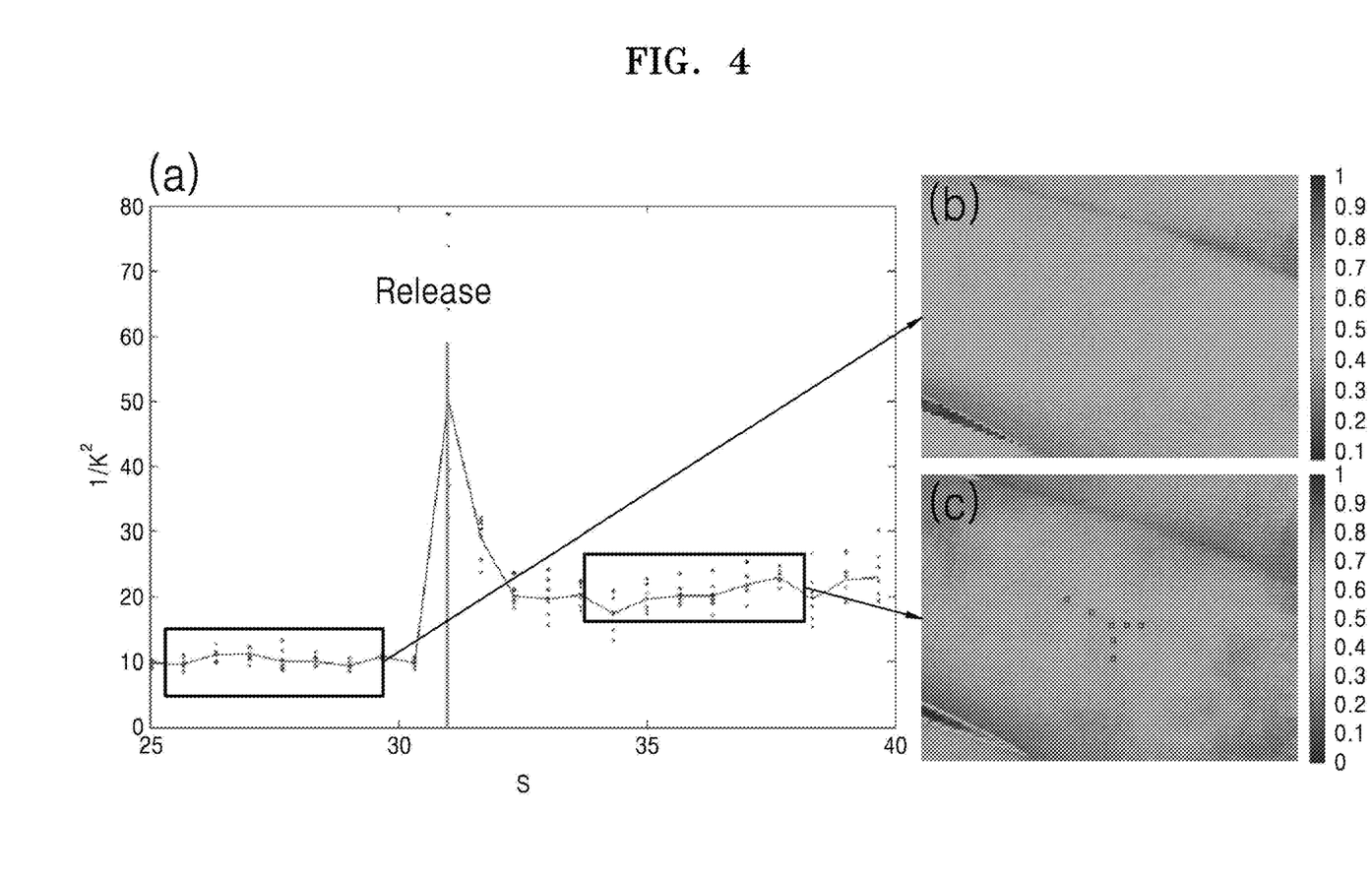
FIG. 4 illustrates a graph and images showing results obtained by measuring a change in a blood flow rate of a human body by using a laser beam having a near-infrared light wavelength band.
Figure 5:
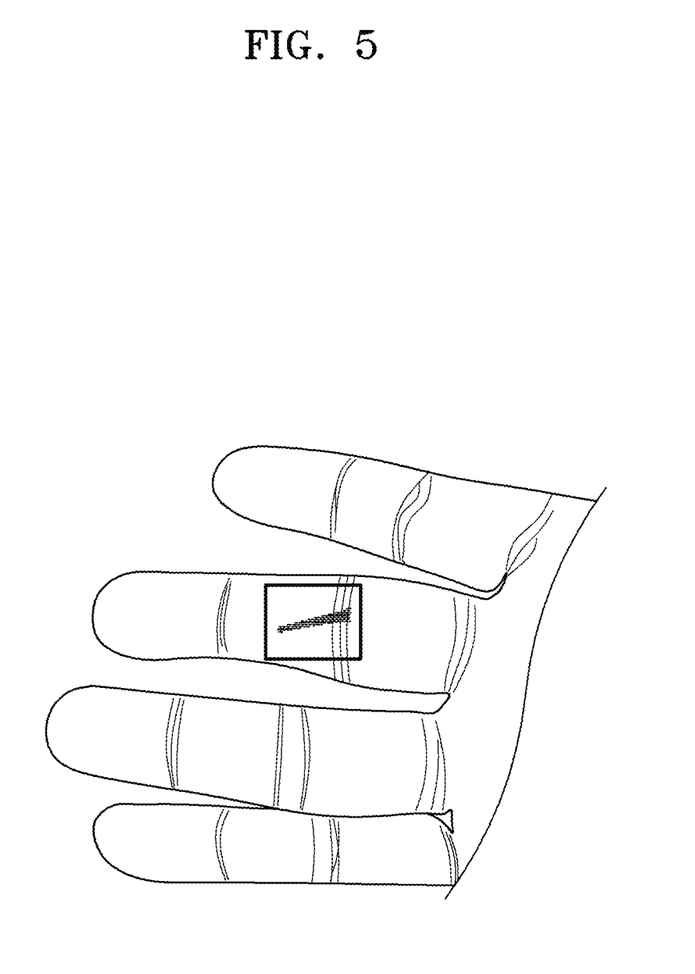
FIG. 5 is a diagram illustrating a position of a finger that is imaged for obtaining the results of FIG. 4.

FIG. 4 illustrates a graph and images showing results obtained by measuring a change in a blood flow rate of a human body by using a laser beam having a near-infrared light wavelength band. FIG. 5 is a diagram illustrating a position of a finger that is imaged in order to obtain the results of FIG. 4.

The graph (a) of FIG. 4 shows a change in speckle contrast as a function of time. The left side of the "Release" axis shows speckle contrast when no blood is flowing, and a right side thereof shows speckle contrast when blood is flowing. The image (b) of FIG. 4 shows a speckle contrast image that corresponds to the time when no blood is flowing. The image (c) of FIG. 4 shows a speckle contrast image that corresponds to the time when blood is flowing.

The measurement of FIG. 4 was performed under the following experimental environmental conditions: a laser exposure time=20 ms, a laser diode=30 mW (power) and 780 nm (wavelength), an imaging lens magnification=0.35, an F-value=16, and the image sensor 35 (CCD)=0.33 inches and 800×600. The subject was contracted and then relaxed by using a sphygmomanometer for about two minutes, and about ten frames of the laser speckle contrast image were temporally used.

Speckle contrast was about 0.31 when no blood was flowing, speckle contrast was about 0.22 when blood was flowing, and a speckle contrast difference (ΔK) was about 29%, which represented a significant difference as between when no blood was flowing and when blood was flowing.

Figure 6:
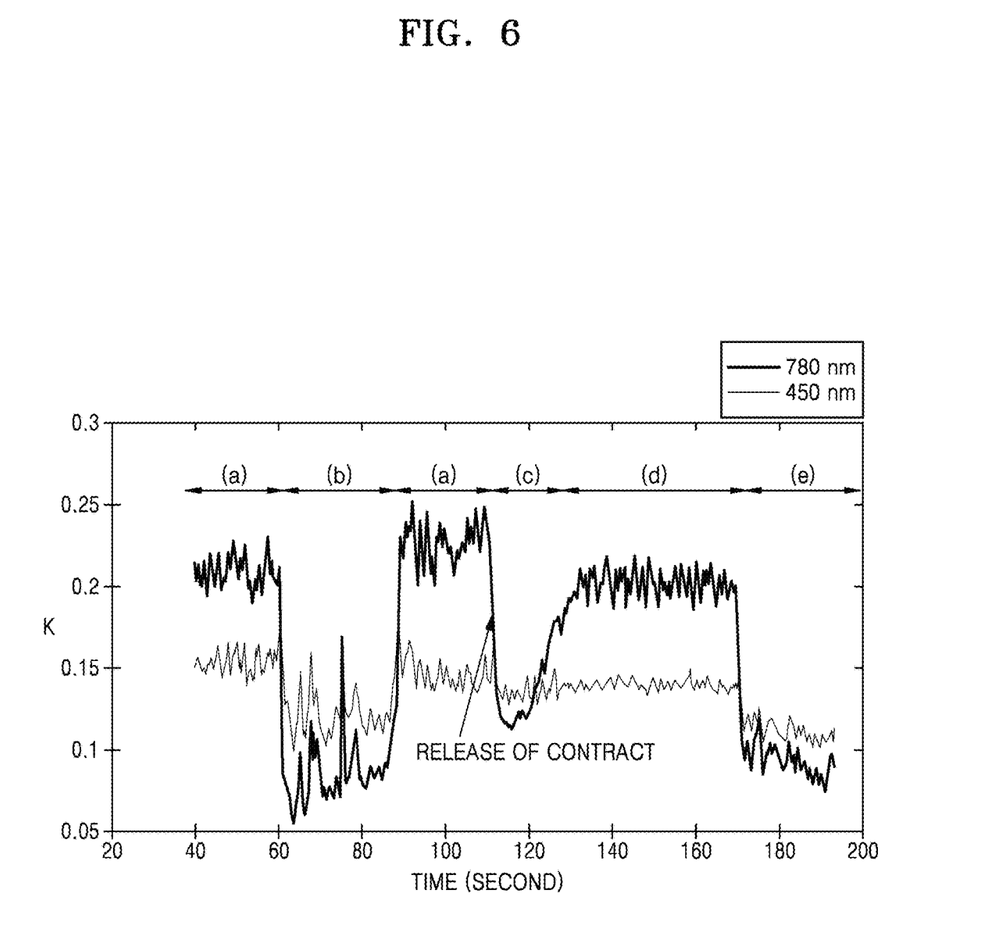
FIG. 6 is a graph showing speckle contrast information recorded according to a time by using a dual wavelength band of a near-infrared light wavelength band and a blue light wavelength band, wherein a blood flow movement state is divided into five sections.

FIG. 6 is a graph showing speckle contrast information recorded as a function of time by using a dual wavelength band of a near-infrared light wavelength band and a blue light wavelength band, wherein a blood flow movement state is divided into five sections.

In FIG. 6, section (a) indicates a state in which the blood flow and the external movement did not exist, section (b) indicates a state in which no blood flow existed but the external movement existed, section (c) indicates in a state in which the contraction has been just released, section (d) indicates a state in which the blood flow existed but no external movement existed, and section (e) indicates in a state in which both the blood flow and the external movement exist.

As is apparent from the graph of FIG. 6, the speckle contrast with respect to the laser beam having the near-infrared light wavelength band decreases due to the external movement and also decreases due to the existence of blood flow and increases in the blood flow rate. Hence, it may be found that the speckle contrast provides information which relates to both the tremor of the surface of the skin and the blood flow rate.

Conversely, as is also apparent from the graph of FIG. 6, it may be found that the speckle contrast with respect to the laser beam having the blue light wavelength band is not substantially affected by the blood flow rate and is predominantly affected by the external movement.

Therefore, when the speckle contrast with respect to the laser beam having the near-infrared light wavelength band is compensated by using the speckle contrast with respect to the laser beam having the blue light wavelength band, it is possible to obtain the speckle contrast in which the noise caused by the external movement is compensated for.

The speckle contrast value with respect to the near-infrared light wavelength band decreases due to the existence of the blood flow or the influence of the external movement. The degree of correlation between the two speckle contrasts is low with respect to the blood flow and is high with respect to the external movement. In this aspect, it may be found that when the value of the sample correlation coefficient is small, the speckle contrast is affected by the blood flow, and when the value of the sample correlation coefficient is large, the speckle contrast is affected by the external movement.

Therefore, when the reference speckle value $K_{th}$, the reference correlation coefficient $C_{th}$, and the compensation coefficient $\beta$ are determined and the speckle contrast with respect to the near-infrared light wavelength band is compensated by using the reference speckle value $K_{th}$, the reference correlation coefficient $C_{th}$, and the compensation coefficient $\beta$, the blood flow rate may be accurately obtained via contrast information even when a strong external movement exists.

Figure 7:
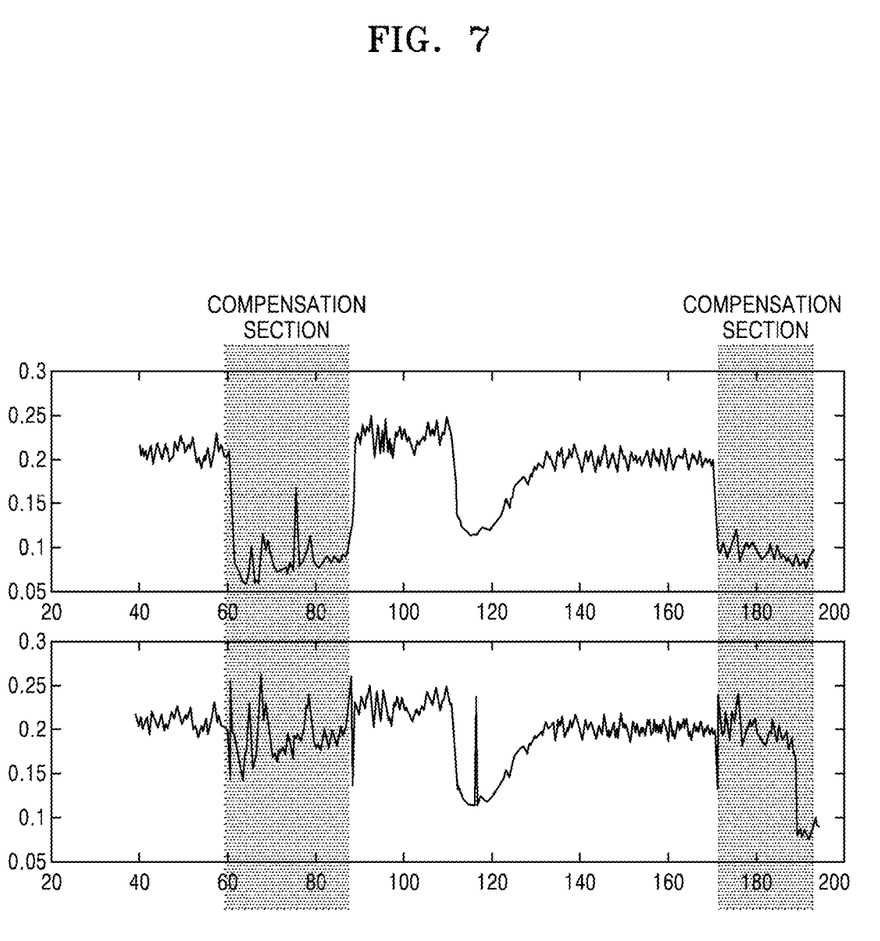
FIG. 7 is a graph showing a compensated speckle contrast with respect to a near-infrared light wavelength band in a section in which an external movement is reflected in record information of FIG. 6.

FIG. 7 is a graph showing compensated speckle contrast with respect to a near-infrared light wavelength band in a section in which an external movement exists in record information of FIG. 6. An upper graph of the FIG. 7 shows the speckle contrast with respect to the near-infrared light wavelength band before compensation, and a lower graph of FIG. 7 shows the compensated speckle contrast in the shaded section (i.e., as indicated by "compensation section" in FIG. 7) in which the external movement exists. The compensated speckle contrast of FIG. 7 was obtained under the following compensation conditions: the reference speckle value $K_{th}$=about 0.13, the reference correlation coefficient $C_{th}$=about 0.8, and the compensation coefficient $\beta$=about 0.8.

Figure 8:
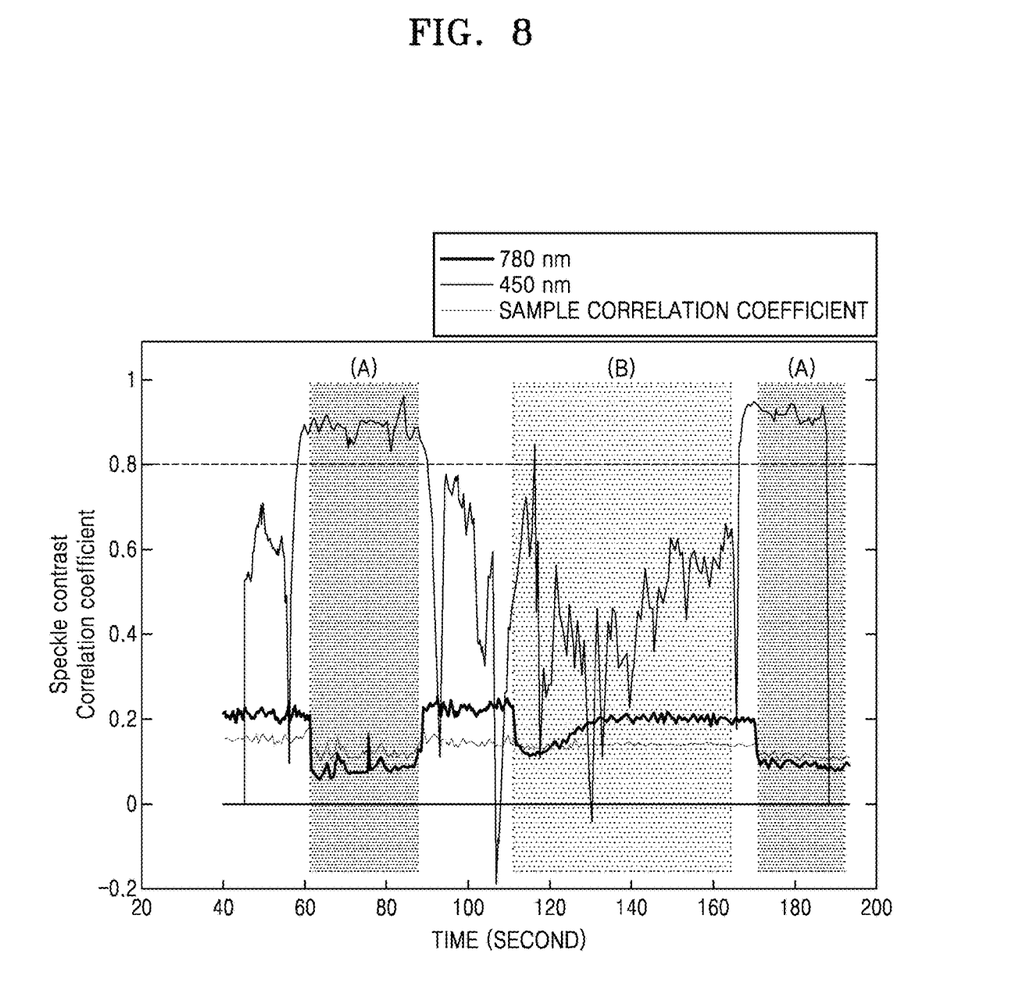
FIG. 8 is a graph showing a correlation between speckle contrasts in the record information of FIG. 6.

FIG. 8 is a graph showing a correlation between speckle contrasts in the record information of FIG. 6. The sample correlation coefficient was calculated by using Formula 3 above. In the graph of FIG. 8, a correlation analysis was performed so as to obtain an association between pieces of contrast information with respect to wavelength bands. A sample of a correlation coefficient between the speckle contrasts was obtained by forming a window every about 60 frames as a function of time.

Referring to FIG. 8, it may be found that the correlation is relatively strong in section (A) in which the speckle contrast with respect to the near-infrared light wavelength band decreases due to the existence of the external movement, and the correlation is relatively weak in section (B) in which the speckle contrast with respect to the near-infrared light wavelength band decreases due to the blood flow without the external movement. Therefore, it may be found that the speckle contrast with respect to the laser beam having the blue light wavelength band has information which relates only the movement of the surface, and it is possible to distinguish the influence of the blood flow from the influence of the external movement, by using the correlation, such as, for example, by setting a threshold with respect to the correlation coefficient value.

As described above, when the laser speckle contrast imaging system 1 according to the exemplary embodiment is applied, it is possible to obtain an excellent speckle contrast image by compensating for noise caused by the external movement even when the noise is continuously generated due to the external condition of the human being and any external movement, such as, for example, a muscle tremor.

According to the laser speckle contrast imaging system, the laser speckle contrast imaging method, and the apparatus including the laser speckle contrast imaging system, the laser beams having a plurality of wavelength bands and different surface transmittances with respect to the subject are irradiated toward the subject, laser speckle images with respect to the wavelength bands are acquired, and a compensated speckle contrast is acquired as an image or a quantified amount by compensating for a change caused by a movement of the subject, thus complementing a limitation that the general laser speckle contrast imaging using a single laser light source is vulnerable to noises caused by the movement of the subject. In addition, since the laser speckle contrast imaging system according to the exemplary embodiment does not need a strong computing power, the laser speckle contrast imaging system may also be applied so as to acquire a biosignal by using a mobile device or the like. Furthermore, the laser speckle contrast imaging system according to the exemplary embodiment may also be easily and additionally applied to apparatuses which include the existing laser speckle contrast imaging system.

It should be understood that exemplary embodiments described herein should be considered in a descriptive sense only and not for purposes of limitation. Descriptions of features or aspects within each exemplary embodiment should typically be considered as being available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A laser speckle contrast imaging system comprising:
   a laser light source configured to irradiate, toward a subject, a first laser beam having a first wavelength band and a first surface transmittance with respect to the subject, and a second laser beam having a second wavelength band and a second surface transmittance with respect to the subject;

wherein the first wavelength band is different than the second wavelength band;
an image capturer comprising an image sensor, the image capturer being configured to acquire a first speckle image of first speckles that are formed when the first laser beam irradiated toward the subject is scattered from the subject, and a second speckle image of second speckles that are formed when the second laser beam irradiated toward the subject is scattered from the subject; and
a signal processor configured to:
convert the first speckle image and the second speckle image respectively into a first speckle contrast image and a second speckle contrast image;
determine a sample correlation coefficient between the first speckle contrast image and the second speckle contrast image; and
when the sample correlation coefficient is less than a threshold, generate a compensated speckle contrast image by compensating the first speckle contrast image for a change caused by a movement of the subject, using the second speckle contrast image.

2. The laser speckle contrast imaging system of claim 1, wherein the first laser beam is adapted to propagate through a surface of the subject, and be scattered by a fluid flowing in the subject, and
the second laser beam is adapted to be scattered from the surface of the subject.

3. The laser speckle contrast imaging system of claim 2, wherein the first speckle contrast image is usable for acquisition of desired information,
the second speckle contrast image is usable for compensation of noise, and
the signal processor is further configured to acquire a third speckle contrast image showing a change in an amount of the fluid by compensating for the noise included in the first speckle contrast image due to the movement of the subject, using the second speckle contrast image.

4. The laser speckle contrast imaging system of claim 1, wherein the first wavelength band comprises a near-infrared light wavelength band, and
the second wavelength band comprises a blue light wavelength band.

5. The laser speckle contrast imaging system of claim 1, wherein the signal processor is further configured to execute a noise compensation algorithm that compensates for noise caused by the movement of the subject.

6. The laser speckle contrast imaging system of claim 5, wherein the first speckle contrast image is usable for acquisition of desired information,
the second speckle contrast image is usable for compensation of the noise, and
the noise compensation algorithm compensates the first speckle contrast image, using the second speckle contrast image, based on the sample correlation coefficient exceeding the threshold.

7. The laser speckle contrast imaging system of claim 1, wherein the image sensor comprises a pixel, and
the laser speckle contrast imaging system further comprises an imaging lens optical system configured to adjust a magnification such that either one or both of the first speckle image and the second speckle image becomes larger than a size of the pixel of the image sensor.

8. The laser speckle contrast imaging system of claim 7, wherein the imaging lens optical system is further configured to adjust the magnification such that either one or both of the first speckle image and the second speckle image has at least twice the size of the pixel of the image sensor.

9. The laser speckle contrast imaging system of claim 1, wherein the laser speckle contrast imaging system is implemented in a mobile device.

10. The laser speckle contrast imaging system of claim 9, wherein the mobile device comprises any one or any combination of a mobile phone, a smart phone, a wristwatch-type device, a tablet device, a personal digital assistant (PDA), a laptop computer, a head mounted display, and a portable media player.

11. The laser speckle contrast imaging system of claim 1, wherein the laser speckle contrast imaging system is implemented in a medical imaging apparatus.

12. The laser speckle contrast imaging system of claim 1, wherein the signal processor is further configured to, based on the sample correlation coefficient being greater than or equal to a threshold, set the first speckle contrast image as the compensated speckle contrast image.

13. A laser speckle contrast imaging method comprising:
irradiating, toward a subject, a first laser beam having a first wavelength band and a first surface transmittance with respect to the subject, and a second laser beam having a second wavelength band and a second surface transmittance with respect to the subject;
wherein the first wavelength band is different than the second wavelength band;
acquiring, by an image sensor, a first speckle image of first speckles that are formed when the first laser beam irradiated toward the subject is scattered from the subject, and a second speckle image of second speckles that are formed when the second laser beam irradiated toward the subject is scattered from the subject;
converting the first speckle image and the second speckle image respectively into a first speckle contrast image and a second speckle contrast image;
determining a sample correlation coefficient between the first speckle contrast image and the second speckle contrast image; and
when the sample correlation coefficient is less than a threshold, generating a compensated speckle contrast image by compensating the first speckle contrast image for a change caused by a movement of the subject, using the second speckle contrast image.

14. The laser speckle contrast imaging method of claim 13, wherein the first speckle contrast image is usable for acquisition of information that relates to a change in a blood flow of the subject,
the second speckle contrast image which is usable for compensation of noise caused by the movement of the subject,
the first wavelength band comprises a near-infrared light wavelength band and is adapted to propagate through a surface of the subject, and be scattered by the blood flow
the second wavelength band comprises a blue light wavelength band and is adapted to be scattered from the surface of the subject, and
wherein the acquiring the compensated speckle contrast image comprises executing a noise compensation algorithm that compensates for the noise caused by the movement of the subject by compensating the first speckle contrast image, using the second speckle contrast image, based on the sample correlation coefficient exceeding the threshold.

15. The laser speckle contrast imaging method of claim 13, wherein the image sensor comprises a pixel, and the laser speckle contrast imaging method further comprises adjusting a magnification such that either one or both of the first speckle image and the second speckle image becomes larger than a size of the pixel of the image sensor.

16. The laser speckle contrast imaging method of claim 15, wherein the adjusting the magnification further comprises adjusting the magnification such that either one or both of the first speckle image and the second speckle image has at least twice the size of the pixel of the image sensor.

* * * * *